United States Patent
Hill et al.

(10) Patent No.: US 10,316,168 B2
(45) Date of Patent: Jun. 11, 2019

(54) POLYETHYLENE COMPOSITIONS WITH IMPROVED OPTICAL PROPERTIES

(71) Applicant: Dow Global Technologies LLC, Midland, MI (US)

(72) Inventors: Martin K. Hill, Tarragona (ES); Selim Bensason, Horgen (CH); Hans-Werner Schmidt, Bayreuth (DE); Paul Smith, Zurich (CH); Seda Aksel, Zurich (CH)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/539,225

(22) PCT Filed: Sep. 17, 2015

(86) PCT No.: PCT/US2015/050688
§ 371 (c)(1),
(2) Date: Jun. 23, 2017

(87) PCT Pub. No.: WO2016/105610
PCT Pub. Date: Jun. 30, 2016

(65) Prior Publication Data
US 2018/0022894 A1 Jan. 25, 2018

(30) Foreign Application Priority Data
Dec. 23, 2014 (EP) .................................... 14382561

(51) Int. Cl.
*C08K 5/1545* (2006.01)
*C08K 5/20* (2006.01)
*C07C 233/57* (2006.01)
*C07C 233/65* (2006.01)
*C08J 5/18* (2006.01)
*C08L 23/06* (2006.01)

(52) U.S. Cl.
CPC .............. *C08K 5/20* (2013.01); *C07C 233/57* (2013.01); *C07C 233/65* (2013.01); *C08J 5/18* (2013.01); *C08L 23/06* (2013.01); *C07C 2601/14* (2017.05); *C07C 2601/16* (2017.05); *C08J 2323/06* (2013.01); *C08L 2201/10* (2013.01); *C08L 2203/16* (2013.01); *C08L 2205/24* (2013.01)

(58) Field of Classification Search
CPC ................................................... C08K 5/1545
See application file for complete search history.

(56) References Cited

U.S. PATENT DOCUMENTS

| | | |
|---|---|---|
| 5,198,484 A | 3/1993 | Mannion |
| 6,005,034 A | 12/1999 | Hayashida et al. |
| 6,235,823 B1 | 5/2001 | Ikeda et al. |
| 7,790,793 B2 | 9/2010 | Schmidt et al. |
| 8,420,721 B2 | 4/2013 | Urushihara et al. |
| 2013/0309515 A1* | 11/2013 | Zheng ....................... B32B 7/12 428/513 |

FOREIGN PATENT DOCUMENTS

| | | |
|---|---|---|
| CA | 2203876 | 4/1997 |
| CN | 1962080 A | 3/2007 |
| CN | 102634119 B | 3/2014 |
| CN | 104004253 A | 8/2014 |
| EP | 0421634 A2 | 4/1991 |
| EP | 0647643 A1 | 4/1995 |
| WO | 0246300 A2 | 6/2002 |
| WO | 2004072168 A2 | 8/2004 |
| WO | 2007127067 A1 | 11/2007 |
| WO | 2015050688 | 9/2015 |

OTHER PUBLICATIONS

Bai et al., "Synergistic Toughening Effects of Nucleating Agent and Ethylene-Octene Copolymer on Polypropylene" Journal of Applied Polymer Science, 2008, pp. 3270-3280, vol. 108, Wiley Periodicals, Inc.
Li et al., "Annealing Induced Microstructure and Fracture Resistance Changes in Isotactic Polypropylene/Ethylene-Octene Copolymer Blends with and without B-Phase Nucleating Agent", Journal of Polymer Science Part B: Polymer Physics, 2010, vol. 48, p. 2108-2120, Wiley Periodicals, Inc.
International Preliminary Report on Patentability pertaining to PCT/US2015/050688 dated Mar. 7, 2017.
International Search Report and Written Opinion pertaining to PCT/US2015/050688 dated Nov. 27, 2015.
European Search Report pertaining to Application No. 14382561.0 dated Mar. 17, 2015.

* cited by examiner

*Primary Examiner* — Robert D. Harlan
(74) *Attorney, Agent, or Firm* — Dinsmore & Shohl LLP

(57) ABSTRACT

Embodiments of a polyethylene composition comprise at least 50% by wt. of at least one polyethylene polymer; and 0.001 to 2% by wt. of bisamide nucleating agent utilized to reduce haze within the polyethylene composition.

20 Claims, No Drawings

POLYETHYLENE COMPOSITIONS WITH IMPROVED OPTICAL PROPERTIES

CROSS REFERENCE TO RELATED APPLICATION

The present application hereby claims the benefit of EPO Patent Application No. 14382561.0 filed Dec. 23, 2014.

FIELD

Embodiments of the present disclosure relate to a polyethylene composition, more particularly, a polyethylene composition yielding improved optical performance via inclusion of a bisamide nucleating agent.

BACKGROUND

Polyethylene compositions and resins are utilized in various applications and articles, for example, in the production of molded articles, blown films, and various other articles. Additives used for increasing the rate of nucleation during crystallization of semi-crystalline polymers are termed nucleators or nucleating agents. The addition of nucleating agents typically increases the overall rate of crystallization, and crystallization temperature of the polymers. This generally translates to faster solidification, and may be used to reduce the cycle time in processes like injection molding. Nucleators may also influence other properties, such as stiffness, toughness, haze, gloss, permeability and shrinkage. Nucleators that improve optical properties like haze and clarity are termed clarifiers. Various organic and/or inorganic additives may serve as nucleators, such as benzoic acids, talc, pigments, sorbitols, phosphate ester derivatives, and other polymeric species.

Derivatives of dibenzylidene sorbitol are well known clarifiers for polypropylene resins and films. The use of clarifiers in polyethylene resins and films is not common, due to much higher rates of crystallization in polyethylene compared to polypropylene, which makes haze reduction and the improvement of optical properties more challenging for polyethylene films and resins. Regarding the use of clarifiers, there is no known correlation between effective haze reduction for polypropylene compositions and effective haze reduction for polyethylene compositions.

Accordingly, there may be a continual need for nucleating agents which increase the rate of crystallization in polyethylene compositions while also reducing the haze and thereby improve the optical properties.

SUMMARY

Embodiments of the present invention are directed to polyethylene compositions having bisamide nucleating agents which reduce haze in the polyethylene compositions while also increasing the rate of crystallization in the polyethylene composition.

According to one embodiment, a polyethylene composition is provided comprising: at least 50% by wt. of at least one polyethylene polymer; and 0.001 to 2% by wt. nucleating agent comprising a structure of formulas (I), (II), or (III):

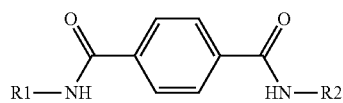

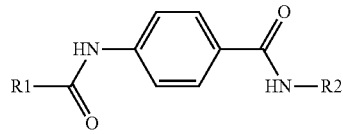

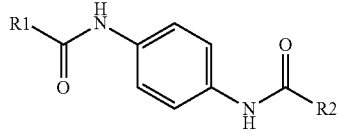

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; (C3-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-C12 cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl; naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl).

DETAILED DESCRIPTION

Embodiments of the present disclosure are directed to polyethylene compositions comprising haze reducing bisamide nucleating agents. Because of the inclusion of bisamide nucleating agents, the present compositions demonstrate high transmittance, high clarity, and low haze.

In specific embodiments, the polyethylene compositions may comprise at least 50% by wt. of at least one polyethylene polymer; and 0.001 to 2% by wt nucleating agent. The polyethylene compositions may comprise a structure of formulas (I), (II), or (III):

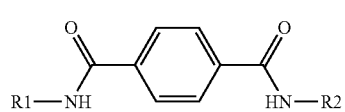

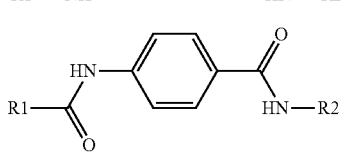

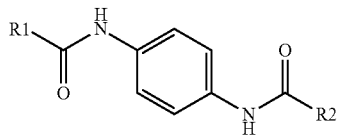
(III)

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; (C3-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-C12 cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl; naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl);

In one embodiment, the R1, R2, or both of the nucleating agent is

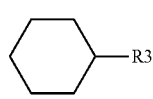

wherein R3 is a direct bond, or a $C_1$-$C_6$ alkyl, or a $C_1$-$C_3$ alkyl.

In another embodiment, the R1, R2 or both of the nucleating agents are

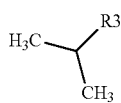

wherein R3 is a direct bond, or a $C_1$-$C_6$ alkyl, or a $C_1$-$C_3$ alkyl.

In a further embodiment, the R1, R2 or both of the nucleating agents are

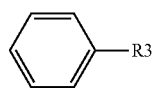

wherein R3 is a direct bond, or a $C_1$-$C_6$ alkyl, or a $C_1$-$C_3$ alkyl.

In yet another embodiment, the R1, R2, or both of the nucleating agents are

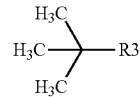

wherein R3 is a direct bond, or a $C_1$-$C_6$ alkyl, or a $C_1$-$C_3$ alkyl.

In yet another embodiment, the R1, R2, or both of the nucleating agents are a $C_1$-$C_6$ alkyl, or a $C_1$-$C_3$ alkyl.

As used herein, "polyethylene composition" means any formulation comprising polyethylene polymer solely or with additional components, such as an additional polymer. As used herein, "polyethylene polymer" refers to a polymer made of 100% ethylene-monomer units, i.e., a homopolymer, or to copolymers produced with other monomeric moieties such as α-olefins, e.g. propylene, 1-butene, 1-pentene, 1-hexene or 1-octene, etc. Various polyethylene polymers are contemplated as suitable. For example and not by way of limitation, the polyethylene polymers may include a high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE), and ultra low density polyethylene (ULDPE), or mixtures thereof.

In one or more embodiments, the polyethylene polymer may have a melt index (I2) ≤50 g/10 min, wherein I2 is measured according to ASTM D1238 at 190° C. and 2.16 kg load, and a density about 0.855 to about 0.970 g/cm$^3$. In other embodiments, the I2 may be ≤25 g/10 min, or ≤10 g/10 min. In further embodiments, the density may be 0.900-0.955 g/cm$^3$, or 0.910-0.940 g/cm$^3$.

For example and not by way of limitation, suitable commercial examples of the LLDPE may include one or more of DOWLEX® 2045 G, DOWLEX® 2552 E, or TUFLIN™ HS-7028 which are available from The Dow Chemical Company, Midland Mich. Other compositions having either homogeneous or heterogeneous short chain branching distributions, or compositions with broad or narrow molecular weight distributions are considered suitable. Various other resins, such as EXCEED™ from ExxonMobil, or EVOLUE™ from Prime Polymer Co., Ltd. are also contemplated.

The polyethylene composition comprises greater than about 50% by wt., or greater than about 60% by wt., or greater than about 70% by wt., or greater than about 80% by wt., or greater than about 90% by wt. of polyethylene polymer. Additionally, the polyethylene composition may comprise about 0.001 to about 2% by wt., or about 0.001 to about 1% by wt., or about 0.005 to about 1% by wt, or about 0.01 to about 0.5% by wt., or about 0.1 to about 0.5% by wt., or 0.01 to about 0.1 wt % of the nucleating agent. Without being bound by theory, haze reduction may vary depending on which R (R1 and R2) groups are utilized in structures I, II, and III. Specifically, the various R groups may have various solubilities inside the polyethylene composition. Unsolubilized nucleating agent may increase haze, thus selecting a concentration which minimizes the amount of unsolubilized nucleating agent may be beneficial.

In one embodiment, the polyethylene composition is substantially free of polypropylene. In additional embodiments, it is contemplated to include further polymers for blending with the polyethylene polymer. For example, it is contemplated to include a blend of multiple polyethylene polymers. Moreover, it is also contemplated to blend the polyethylene polymers with a polypropylene polymer. For example, it is contemplated that a second polymer may be included in amounts from about 0.5 to about 45% by wt., or about 1 to about 25% by wt., or about 5 to about 15% by wt.

The polyethylene composition may be formed into various articles. For example, the article may be a blown film, a cast film, or a molded article (for example, injection molding, or rotational molding). The articles may be extruded or formed into various extruded profiles such as sheets, pipes, or tubes. Moreover, in further embodiments, the articles may be melt-spun fibers. Upon inclusion of the present bisamide nucleating agents, the article may achieve a haze value reduction of at least 15% when compared to an article having the same polyethylene polymer but without the bisamide nucleating agent. In further embodiment, the article may achieve a haze reduction of at least 20%, or at least 25%, or at least 30%, or at least 35%, or at least 40% when compared to an article having the same polyethylene polymer but without the bisamide nucleating agent. Various dimensions and thicknesses are contemplated for the polyethylene articles. The articles may comprise a thickness of 0.001 mm to about 5 mm, or about 0.5 mm to about 2.5 mm, or about 0.5 mm to about 1.5 mm.

Various procedures are contemplated for producing the present composition. For example and not by way of limitation, these procedures may include standard procedures such as mixing the prescribed components in a conventional mixer and/or melting, kneading, and/or extruding the mixture.

Additional optional materials may be added to the compositions of the present disclosure. For example, these materials may include antioxidants, antibacterial agents, ultraviolet absorbers, light stabilizers, neutralizers, antistatic agents, antiblocking agents, flame retardants, lubricants, various other processing aids and fillers, and the like and mixtures thereof. Additional information on the optional materials is provided in U.S. Pat. No. 7,790,793, which is incorporated by reference herein in its entirety.

EXAMPLES

Part A: Preparation of Bisamide Nucleating Agents

The following lists exemplary bisamide structures and method of making.

Example 1: Method of Making N,N'-Dicyclohexyl-1,4-benzenedicarboxamide

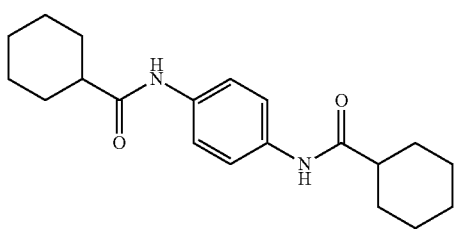 [SMILES: O=C(Nc1ccc(NC(=O)C2CCCCC2)cc1)C1CCCCC1]

N-methylpyrrolidone (NMP) was stirred for 1 day over $CaH_2$ and finally distilled off. Triethylamine was treated in a similar manner. Cyclohexylamine was stirred over KOH and distilled off. 5.5 mL of cyclohexylamine, 0.1 g of anhydrous LiCl, and 25 mL of triethylamine were dissolved in 100 mL of dry NMP under inert atmosphere. 4.06 g of terephthaloyl chloride were added to the solution and subsequently stirred for 2 h at 75° C. Then the solution was cooled to room temperature and poured into ice-water. The precipitate was filtered off, washed several times with water. The crude product was recrystallized from DMF, yielding 4.03 g of N,N'-Dicyclohexyl-1,4-benzenedicarboxamide as white powder.

Example 2: N,N'-Bis(cyclohexylmethyl)-1,4-benzenedicarboxamide

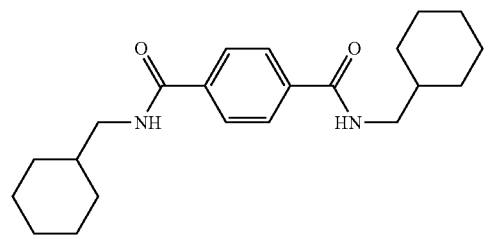 [SMILES: O=C(NCC1CCCCC1)c1ccc(C(=O)NCC2CCCCC2)cc1]

Triethylamine was stirred for 1 day over $CaH_2$ and finally distilled off. Tetrahydrofuran (THF) was refluxed for three days over $CaH_2$, distilled, refluxed for another three days over potassium and finally distilled again. 3.75 mL of cyclohexyanemethylamine, 0.1 g of anhydrous LiCl, and 15 mL of triethylamine were dissolved in 150 mL of dry THF under inert atmosphere and cooled to 0° C. 2.66 g of terephthaloyl chloride were added to the solution and subsequently refluxed for 12 h. Then the solution was cooled to room temperature and poured into ice-water. The precipitate was filtered off, washed several times with water. The crude product was recrystallized from DMSO, yielding 4.25 g of N,N'-Bis(cyclohexylmethyl)-1,4-benzenedicarboxamide as white needles.

Example 3: N,N'-Bis(cyclohexylethyl)-1,4-benzenedicarboxamide

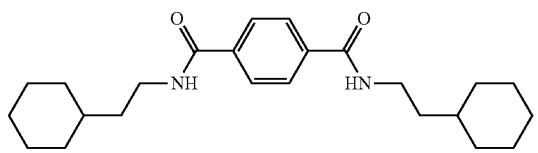 [SMILES: O=C(NCCC1CCCCC1)c1ccc(C(=O)NCCC2CCCCC2)cc1]

Triethylamine was stirred for 1 day over $CaH_2$ and finally distilled off. THF was refluxed for three days over $CaH_2$, distilled, refluxed for another three days over potassium and finally distilled again. 3.25 mL of cyclohexyaneethylamine, 0.1 g of anhydrous LiCl, and 15 mL of triethylamine were dissolved in 150 mL of dry THF under inert atmosphere and cooled to 0° C. 2.03 g of terephthaloyl chloride were added to the solution and subsequently refluxed for 12 h. Then the solution was cooled to room temperature and poured into ice-water. The precipitate was filtered off, washed several times with water. The crude product was recrystallized from DMSO, yielding 3.79 g of N,N'-Bis(cyclohexylethyl)-1,4-benzenedicarboxamide as white needles.

Example 4: N,N'-Bis(isopropyl)-1,4-benzenedicarboxamide

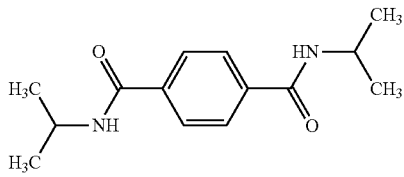 [SMILES: CC(C)NC(=O)c1ccc(C(=O)NC(C)C)cc1]

Triethylamine was stirred for 1 day over CaH$_2$ and finally distilled off. THF was refluxed for three days over CaH$_2$, distilled, refluxed for another three days over potassium and finally distilled again. 2.77 mL of isopropylamine, 0.1 g of anhydrous LiCl, and 15 mL of triethylamine were dissolved in 100 mL of dry THF under inert atmosphere and cooled to 0° C. 3.00 g of terephthaloyl chloride were added to the solution and subsequently refluxed for 12 h. Then the solution was cooled to room temperature and poured into ice-water. The precipitate was filtered off, washed several times with water. The crude product was recrystallized from methanol, yielding 2.40 g of, N'-Bis(isopropyl)-1,4-benzenedicarboxamide as white crystals.

Example 5: N,N'-Bis(2-methylpropyl)-1,4-benzenedicarboxamide

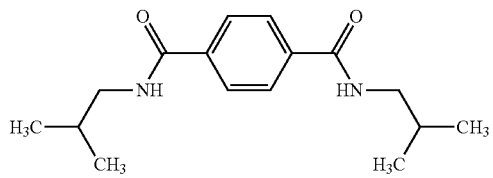 [SMILES: CC(C)CNC(=O)c1ccc(C(=O)NCC(C)C)cc1]

Triethylamine was stirred for 1 day over CaH$_2$ and finally distilled off. THF was refluxed for three days over CaH$_2$, distilled, refluxed for another three days over potassium and finally distilled again. 3.26 mL of isobutylamine, 0.1 g of anhydrous LiCl, and 15 mL of triethylamine were dissolved in 100 mL of dry THF under inert atmosphere and cooled to 0° C. 3.00 g of terephthaloyl chloride were added to the solution and subsequently refluxed for 12 h. Then the solvent was evaporated, the residue was dissolved in MeOH, and poured into ice-water. The precipitate was filtered off, washed several times with water, yielding 2.09 g of N,N'-Bis(2-methylpropyl)-1,4-benzenedicarboxamide as white powder.

Example 6: N,N'-Bis(2-methylbutyl)-1,4-benzenedicarboxamide

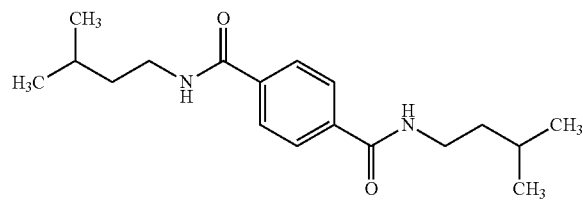 [SMILES: CC(C)CCNC(=O)c1ccc(C(=O)NCCC(C)C)cc1]

Triethylamine was stirred for 1 day over CaH$_2$ and finally distilled off. THF was refluxed for three days over CaH$_2$, distilled, refluxed for another three days over potassium and finally distilled again. 3.35 mL of 3-methylbutylamine, 0.1 g of anhydrous LiCl, and 15 mL of triethylamine were dissolved in 100 mL of dry THF under inert atmosphere and cooled to 0° C. 2.66 g of terephthaloyl chloride were added to the solution and subsequently refluxed for 12 h. Then the solution was cooled to room temperature and poured into ice-water. The precipitate was filtered off, washed several times with water. The crude product was recrystallized from DMSO, yielding 2.98 g of N,N'-Bis(2-methylbutyl)-1,4-benzenedicarboxamide as white powder.

Example 7: N,N'-Bis(tert-butyl)-1,4-benzenedicarboxamide

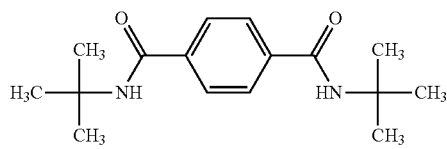

NMP was stirred for 1 day over CaH$_2$ and finally distilled off. Triethylamine was treated in a similar manner. 5.04 mL of tert-butylamine, 0.1 g of anhydrous LiCl, and 25 mL of triethylamine were dissolved in 100 mL of dry NMP under inert atmosphere. 4.06 g of terephthaloyl chloride were added to the solution and subsequently stirred for 2 h at 75° C. Then the solution was cooled to room temperature and poured into ice-water. The precipitate was filtered off, washed several times with water. The crude product was recrystallized from DMF, yielding 3.68 g of N,N'-Bis(tert-butyl)-1,4-benzenedicarboxamide as whitish needles.

Example 8: N,N'-Bis(2,2-dimethylpropyl)-1,4-benzenedicarboxamide

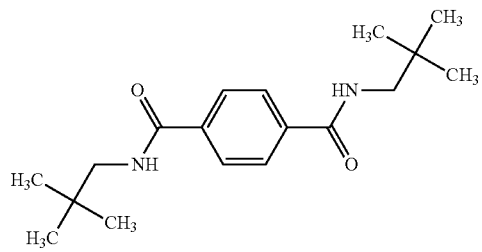 [SMILES: CC(C)(C)CNC(=O)c1ccc(C(=O)NCC(C)(C)C)cc1]

Triethylamine was stirred for 1 day over CaH$_2$ and finally distilled off. THF was refluxed for three days over CaH$_2$, distilled, refluxed for another three days over potassium and finally distilled again. 3.17 mL of amylamine, 0.1 g of anhydrous LiCl, and 12 mL of triethylamine were dissolved in 70 mL of dry THF under inert atmosphere and cooled to 0° C. 2.50 g of terephthaloyl chloride were added to the solution and subsequently refluxed for 12 h. Then the solvent was evaporated, the residue was dissolved in MeOH, and poured into ice-water. The precipitate was filtered off, washed several times with water and hexane and dried in vacuum, yielding 3.23 g of N,N'-Bis(2,2-dimethylpropyl)-1,4-benzenedicarboxamide as white powder.

Example 9: N,N'-Bis(3,3-dimethylbutyl)-1,4-benzenedicarboxamide

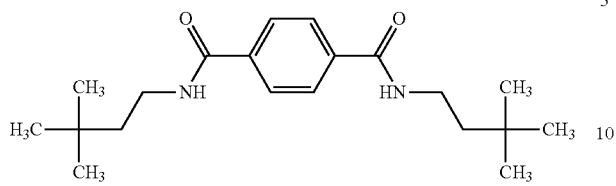

Triethylamine was stirred for 1 day over $CaH_2$ and finally distilled off. THF was refluxed for three days over $CaH_2$, distilled, refluxed for another three days over potassium and finally distilled again. 1.33 mL of 3,3-dimethylbutylamine, 0.1 g of anhydrous LiCl, and 5 mL of triethylamine were dissolved in 50 mL of dry THF under inert atmosphere and cooled to 0° C. 0.91 g of terephthaloyl chloride were added to the solution and subsequently refluxed for 12 h. Then the solvent was evaporated, the residue was dissolved in MeOH, and poured into water. The precipitate was filtered off, washed several times with water and dried in vacuum. Recrystallization from methanol yields 1.04 g of N,N'-Bis (3,3-dimethylbutyl)-1,4-benzenedicarboxamide as white powder.

Example 10: N,N'-Dipropyl-1,4-benzenedicarboxamide

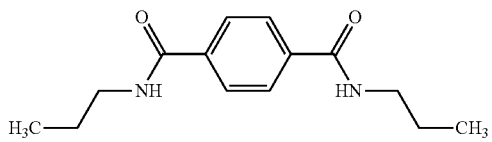

Triethylamine was stirred for 1 day over $CaH_2$ and finally distilled off. THF was refluxed for three days over $CaH_2$, distilled, refluxed for another three days over potassium and finally distilled again. 2.67 mL of propylamine, 0.1 g of anhydrous LiCl, and 15 mL of triethylamine were dissolved in 100 mL of dry THF under inert atmosphere and cooled to 0° C. 3.00 g of terephthaloyl chloride were added to the solution and subsequently refluxed for 12 h. Then the solution was cooled to room temperature and poured into water. The precipitate was filtered off, washed several times with water. The crude product was recrystallized from methanol yielding 1.5 g of N,N'-Dipropyl-1,4-benzenedicarboxamide as yellowish needles.

Part B: Preparation of Polymer Resin Plaques with Bisamide Nucleating Agents

The influence of bisamide nucleating agents on haze was examined for three linear low density polyethylenes from The Dow Chemical Company.

TABLE 1

| | LLDPE Properties | |
|---|---|---|
| Name | Density (g/cc) | Melt Index [2.16 kg, 190° C.] (g/10 min) |
| DOWLEX 2045G | 0.920 | 1 |
| DOWLEX 2552E | 0.920 | 25 |
| TUFLIN HS-7028 NT7 | 0.918 | 1 |

DOWLEX 2045G is an ethylene-octene copolymer suitable for blown film applications. DOWLEX 2552E is an ethylene-octene copolymer suitable for injection molding and fiber applications. DOWLEX HS7028 NT7 is an ethylene-hexene copolymer suitable for blown film applications. Density was measured per ASTM D792, the melt index per ASTM D1238.

Small-Scale Compounding and Injection Molding for Haze Measurements

Blends of the polyethylene resins with the nucleators were prepared in a laboratory co-rotating mini-twin-screw extruder (Xplore from DSM, 15.0 ml volume) at 40 r.p.m. for 5 min at 220° C., in a nitrogen blanket. First, a masterbatch of 2% by weight of the nucleator was made in the polyethylene resin. This masterbatch was diluted and re-compounded with neat polyethylene resin to achieve the desired final concentration of the nucleator in the polymer. The melt from the extruder was injected into a circular mold kept at room temperature to produce plaques of 1.0 mm thickness and 25.0 mm diameter.

Haze Measurements for Molded Samples

The haze of the injection-molded samples was determined at room temperature with a Haze-Gard Plus® instrument (BYK Gardner GmbH, Germany) according to ASTM standard D1003. A circular area on the plaque samples, 18.0 mm in diameter, was illuminated by the light beam; the recorded haze values are referred to as "overall-area haze". In addition, haze values of a circular area with 8.0 mm diameter on samples (those free of surface irregularities) were recorded and are referred to as "small-area haze". In order to eliminate the effect of surface scattering, "bulk haze" measurements were conducted by filling a 50.0×45.0×2.5 mm cuvette, (AT-6180 from BYK Gardner GmbH, Germany) with non-drying immersion oil (Cargille Series A refractive index oil of n=1.5150±0.0002) and inserting samples therein. Haze values reported here correspond to the average of values from five measurements.

Haze Data

Haze data for injection molded plaques of compounds made for N,N'-bis(cyclohexylmethyl)-1,4-phenylene dicarboxamide (BCPCA) with DOWLEX 2045G, DOWLEX 2552E and TUFLIN HS 7028 NT7 are given below.

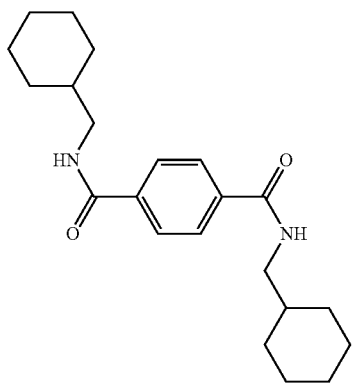 [SMILES: O=C(NCC1CCCCC1)c1ccc(C(=O)NCC2CCCCC2)cc1]

TABLE 2

TUFLIN HS7028 NT7/BCPCA compositions

| Concentration (% w/w) | Overall-area haze (%) | Small-area haze (%) | Bulk haze (%) |
|---|---|---|---|
| 0 | 80.0 | n/a | 54.0 |
| 0.01 | 74.8 | n/a | 48.6 |
| 0.05 | 74.2 | n/a | 46.8 |
| 0.08 | 74.3 | n/a | 46.7 |
| 0.1 | 74.5 | n/a | 45.0 |
| 0.15 | 72.1 | n/a | 42.0 |
| 0.2 | 69.6 | n/a | 35.0 |
| 0.5 | 77.2 | n/a | 48.0 |

TABLE 3

DOWLEX 2045G/BCPCA compositions

| Concentration (% w/w) | Overall-area haze (%) | Small-area haze (%) | Bulk haze (%) |
|---|---|---|---|
| 0 | 73.0 | 60.0 | 62.0 |
| 0.01 | 82.0 | 72.7 | n/a |
| 0.05 | 81.3 | 70.9 | 68.0 |
| 0.08 | 70.8 | 53.0 | 49.3 |
| 0.1 | 62.7 | 33.8 | 37.5 |
| 0.15 | 59.2 | 32.6 | 29.8 |
| 0.2 | 64.0 | 33.8 | n/a |
| 0.5 | 72.4 | 47.6 | n/a |

TABLE 4

DOWLEX 2552E/BCPCA compositions

| Concentration (% w/w) | Overall-area haze (%) | Small-area haze (%) | Bulk haze (%) |
|---|---|---|---|
| 0 | 90.0 | 88.0 | 88.0 |
| 0.01 | 89.8 | 87.5 | 88.3 |
| 0.05 | 90.6 | 88.0 | 88.8 |
| 0.1 | 49.8 | 35.0 | 44.4 |
| 0.2 | 60.6 | 46.0 | 54.9 |
| 0.5 | 70.0 | 54.5 | 64.2 |
| 1 | 81.6 | 70.0 | 76.6 |

The following includes haze data for DOWLEX 2552E with various nucleators.

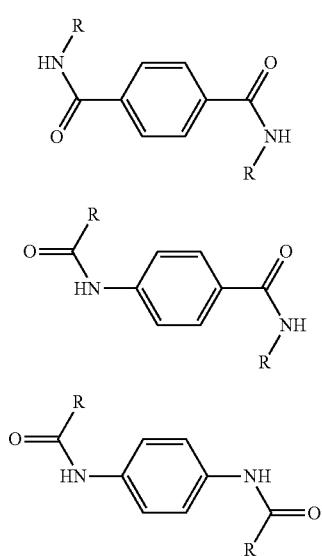

Table 5: Where substituent R is cyclohexyl for the table below.

| Concentration (% w/w) | Compound A | Compound B | Compound C |
|---|---|---|---|
| | Overall-area haze (%) | | |
| 0 | 90.0 | 90.0 | 90.0 |
| 0.002 | 89.8 | 89.0 | 89.6 |
| 0.005 | 89.7 | 89.9 | 90.4 |
| 0.01 | 89.7 | 90.3 | 90.7 |
| 0.025 | 91.0 | 91.0 | 93.0 |
| 0.05 | 92.3 | 91.9 | 83.7 |
| 0.1 | 78.2 | 80.0 | 82.0 |
| 0.2 | 78.2 | 75.4 | 87.0 |
| 0.5 | 79.7 | 73.3 | 94.0 |
| 1 | 91.8 | 84.9 | 98.0 |

Table 6: Where substituent R is cyclohexylmethyl for the table below.

| Concentration (% w/w) | Compound A | Compound B | Compound C |
|---|---|---|---|
| | Overall-area haze (%) | | |
| 0 | 90.0 | 90.0 | 90.0 |
| 0.002 | 88.0 | 89.4 | 88.7 |
| 0.005 | 88.6 | 89.5 | 88.9 |
| 0.01 | 89.8 | 89.9 | 89.4 |
| 0.025 | 89.9 | 90.9 | 90.4 |
| 0.05 | 90.6 | 91.8 | 78.7 |
| 0.1 | 49.8 | 92.1 | 65.6 |
| 0.2 | 60.6 | 92.7 | 78.0 |
| 0.5 | 70.0 | 92.4 | 97.4 |
| 1 | 81.6 | 97.0 | 100 |

Table 7: Where substituent R is cyclohexylethyl for the table below.

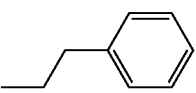

| Concentration (% w/w) | Compound A | Compound B | Compound C |
|---|---|---|---|
| | Overall-area haze (%) | | |
| 0 | 90.0 | 90.0 | 90.0 |
| 0.002 | 88.4 | 89.1 | 89.1 |
| 0 | 90.0 | 90.0 | 90.0 |
| 0.005 | 89.1 | 89.6 | 89.6 |
| 0.01 | 89.4 | 90.5 | 89.9 |
| 0.025 | 90.2 | 90.6 | 90.7 |
| 0.05 | 90.4 | 92.2 | 82.0 |
| 0.1 | 58.6 | 92.5 | 69.3 |
| 0.2 | 56.0 | 93.1 | 79.0 |
| 0.5 | 68.5 | 90.9 | 95.3 |
| 1 | 82.7 | 98.8 | 100 |

Table 8: Where substituent R is n-propyl for the table below.

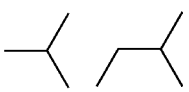

| Concentration (% w/w) | Compound A | Compound B | Compound C |
|---|---|---|---|
| | Overall-area haze (%) | | |
| 0 | 90.0 | 90.0 | 90.0 |
| 0.002 | 88.6 | 89.6 | 89.0 |
| 0.005 | 89.0 | 90.7 | 89.7 |
| 0.01 | 90.0 | 90.9 | 90.5 |
| 0.025 | 90.8 | 91.4 | 92.2 |
| 0.05 | 76.2 | 92.2 | 77.4 |
| 0.1 | 81.8 | 92.5 | 80.7 |
| 0.2 | 85.5 | 91.7 | 81.6 |
| 0.5 | 91.2 | 86.9 | 89.6 |
| 1 | 94.1 | 89.0 | 94.3 |

Haze Data for DOWLEX 2552E with Compound A—and various other R groups is provided in table 9 below.

TABLE 9

| Concentration (% w/w) | R group attached to Compound A | | | | |
|---|---|---|---|---|---|
| | 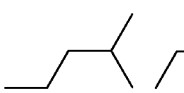 | | | | |
| 0 | 90.0 | 90.0 | 90.0 | 90.0 | 90.0 |
| 0.002 | 89.1 | 89.9 | 89.5 | 89.7 | 89.0 |
| 0.005 | 89.5 | 90.3 | 90.5 | 90.2 | 89.0 |
| 0.01 | 90.1 | 91.0 | 91.0 | 90.5 | 90.0 |
| 0.025 | 90.4 | 91.9 | 91.4 | 91.3 | 90.5 |
| 0.05 | 67.5 | 70.4 | 92.9 | 91.9 | 91.5 |
| 0.1 | 71.5 | 74.9 | 72.1 | 76.5 | 92.0 |
| 0.2 | 79.8 | 78.1 | 80.9 | 80.4 | 79.0 |
| 0.5 | 87.6 | 84.4 | 87.7 | 83.3 | 70.0 |
| 1 | 93.3 | 90.3 | 93.4 | 92.2 | 67.0 |
| 2 | 99.2 | 96.8 | 97.2 | 97.3 | 69.0 |

Part C: Polyethylene Film

Compounds were prepared with DOWLEX 2045G and BCPCA as follows: the respective amounts of additive and base polymer were put into a plastic bag and thoroughly mixed by turning the bag. The powder mixtures were extruded on a twin screw extruder (Leistritz ZSE MAXX, screw diameter=27 mm; screw l/d ratio=48). Before extruding the additive mixtures the extruder was cleaned with standard LDPE and after that with 2 kg of the base polymer. Processing parameters: Cylinder temperature: 170° C. (all heating zones), screw speed: 300-400 U/min, output: 25-30 kg/h. The extruded strands were cooled in a water bath and cut with a pelletizer. The obtained granulate was mixed in a mixer and packed into PE plastic bags.

Exemplary monolayer polyethylene films comprising the DOWLEX 2045G and BCPCA compounds were produced on a monolayer blown film line. Additional process parameters are provided in Table 10 below, and haze results are provided in Table 11 below.

TABLE 10

| Process Parameter | Process Parameter Value |
|---|---|
| Screw diameter | 30 mm |
| Screw length | 25 D |
| Annular die size | 60 mm |
| Die gap | 1.2 mm |
| Melt temperature | 200° C. |
| Blow-up ratio | 2.5 |
| Film thickness | 50 μm |
| Output rate | 5 kg/hr |

Haze was measured based on the ASTM D1003-11 norm using "Hazeguard Plus 4725" test equipment. Haze values given are the average of 5 separate measurements. Samples were allowed to age for minimum 40 hr prior to testing.

TABLE 11

| Film Composition | Average Haze % |
|---|---|
| DOWLEX 2045G - reference | 11.6 |
| DOWLEX 2045G + 300 ppm bisamide | 7.1 |
| DOWLEX 2045G + 500 ppm bisamide | 7.1 |
| DOWLEX 2045G + 800 ppm bisamide | 7.5 |

Part D: Comparison to Trisamide Clarifier

For polypropylene films, trisamide derivatives have demonstrated improvements in optical properties, such as haze reduction; however, they have not demonstrated the same level of improvement in polyethylene films.

The following table depicts the haze reduction yielded by tris(cyclohexylmethyl)-1,3,5-phenylene dicarboxamide (TCPCA) and BCPCA when incorporated into a DOWLEX 2552E LLDPE plaque having a thickness of 1 mm. As shown, the haze-reducing effect of a trisamide was compared to a bisamide, which has the same R-group moieties. Various haze measurements were conducted at increasing concentrations up to 2% of the bisamide and trisamide, and the minimum haze in the concentration range was provided below. As shown, at 0.1% concentration, there is a haze reduction of over 40% (90.0-49.8=40.2%).

TABLE 12

| | BCPCA | TCPCA |
|---|---|---|
| Concentration (% w/w) | Overall-area haze (%) | |
| 0 | 90.0 | 90.0 |
| 0.002 | 88.0 | n/a |
| 0.005 | 88.6 | 88.5 |
| 0.01 | 89.8 | 89.2 |
| 0.025 | 89.9 | 89.7 |
| 0.05 | 90.6 | 78.6 |
| 0.1 | 49.8 | 75.3 |
| 0.2 | 60.6 | 76.9 |
| 0.5 | 70.0 | 82.0 |
| 1 | 81.6 | 90.3 |
| 2 | 95.9 | 96.3 |

It is further noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present disclosure.

It will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these aspects.

The invention claimed is:

1. A polyethylene composition comprising:
   at least 50% by wt. of a linear low density polyethylene polymer (LLDPE); and
   0.001 to 2% by wt nucleating agent comprising a structure of formulas (I), (II), or (III):

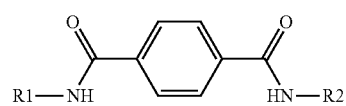
(I)

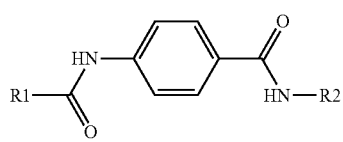
(II)

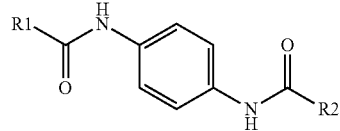
(III)

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; (C3-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-C12 cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl; naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl);

wherein, when the polyethylene composition is used to form an article, the article has a haze value reduction of at least 15% when compared to an article having the same polyethylene polymer but free of the nucleating agent.

2. The polyethylene composition of claim 1 wherein the polyethylene polymer is copolymer of ethylene with alpha-olefin copolymers, an ethylene homopolymer or combinations thereof.

3. The polyethylene composition according to claim 1 wherein the polyethylene composition has a melt index ($I_2$)≤50 g/10 min, wherein $I_2$ is measured according to ASTM D1238 at 190° C. and 2.16 kg load, and a density about 0.855 to about 0.970 g/cm$^3$.

4. The polyethylene composition according to claim 1 wherein the polyolefin resin comprises 0.01-0.5% by wt of the nucleating agent.

5. The polyethylene composition according to claim 1 wherein R1, R2, or both are

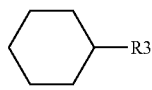

wherein R3 is a direct bond, or a $C_1$-$C_6$ alkyl.

6. The polyethylene composition according to claim 1 wherein R1, R2 or both are

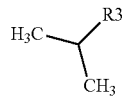

wherein R3 is a direct bond, or a $C_1$-$C_6$ alkyl.

7. The polyethylene composition according to claim 1 wherein R1, R2, or both are

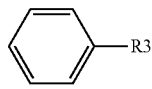

wherein R3 is a direct bond, or a $C_1$-$C_6$ alkyl.

8. The polyethylene composition according to claim 1 wherein R1, R2, or both are

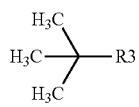

wherein R3 is a direct bond, or a $C_1$-$C_6$ alkyl.

9. The polyethylene composition according to claim 1 wherein R1, R2, or both are a $C_1$-$C_6$ alkyl.

10. The polyethylene composition according to claim 1 wherein the polyethylene composition comprises greater than about 60% by wt.

11. An article produced from the polyethylene composition of any of the preceding claims, wherein the article has a haze value reduction of at least 20% when compared to an article having the same polyethylene polymer but free of the nucleating agent.

12. The article of claim 11 wherein the article is chosen from a blown film, a cast film, a molded article, a melt-spun fiber, or an extruded article, wherein the extruded article is chosen form sheets, pipes, or tubes.

13. The polyethylene according to claim 1 wherein said polyethylene composition has a density of about 0.910 to about 0.940 g/cm$^3$.

14. The polyethylene according to claim 1 wherein the polyethylene composition is substantially free of polypropylene.

15. The polyethylene according to claim 1 wherein polyethylene composition comprises 0.5% by weight to 15% by weight polypropylene.

16. The polyethylene according to claim 1 further comprising from about 0.5 to about 45% of a second polymer, the second polymer comprising a low density polyethylene polymer (LDPE), a high density polyethylene polymer (HDPE), very low density polyethylene (VLDPE), and ultra-low density polyethylene (ULDPE), polypropylene, or combinations thereof.

17. A polyethylene composition comprising:
at least 50% by wt. of at least one polyethylene polymer chosen from a linear low density polyethylene polymer (LLDPE), a low density polyethylene polymer (LDPE), a high density polyethylene polymer (HDPE), or combinations thereof; and
0.001 to 2% by wt nucleating agent comprising a structure of formulas (I), (II), or (III):

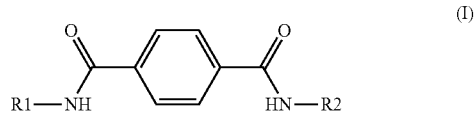

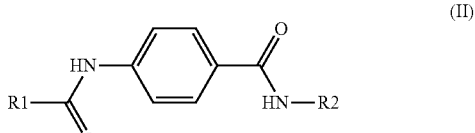

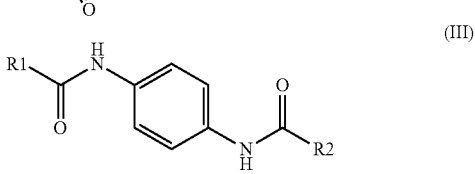

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; (C3-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-C12 cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl; naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl);

provided that when the nucleating agent is a structure of formula (II), R1 and R2 are not cyclohexyl;

wherein, when the polyethylene composition is used to form an article, the article has a haze value reduction of at least 15% when compared to an article having the same polyethylene polymer but free of the nucleating agent.

18. The polyethylene composition according to claim 17, wherein when the nucleating is according to formula (I) and (III), R1, R2, or both are

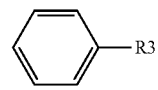

wherein R3 is a direct bond, or a $C_1$-$C_6$ alkyl or when the nucleating agent is according to formula (II), R1, R2, or both are

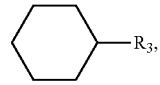

wherein R3 is a $C_1$-$C_6$ alkyl.

19. The polyethylene composition according to claim 17, wherein R1, R2 or both are

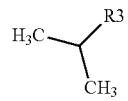

wherein R3 is a direct bond, or a $C_1$-$C_6$ alkyl.

20. The polyethylene composition according to claim 17, wherein R1, R2, or both are

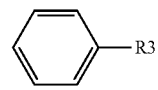

wherein R3 is a direct bond, or a $C_1$-$C_6$ alkyl.

* * * * *

UNITED STATES PATENT AND TRADEMARK OFFICE
CERTIFICATE OF CORRECTION

| | | |
|---|---|---|
| PATENT NO. | : 10,316,168 B2 | Page 1 of 4 |
| APPLICATION NO. | : 15/539225 | |
| DATED | : June 11, 2019 | |
| INVENTOR(S) | : Martin K. Hill et al. | |

It is certified that error appears in the above-identified patent and that said Letters Patent is hereby corrected as shown below:

Column 47, Claim 2:
Reads:
2. The polyethylene composition of claim 1 wherein the polyethylene polymer is copolymer of ethylene with alpha-olefin copolymers, an ethylene homopolymer or combinations thereof.

Should Read:
2. The polyethylene composition of claim 1 wherein the polyethylene polymer is a copolymer of ethylene with alpha-olefin copolymers, an ethylene homopolymer or combinations thereof.

Column 18, Claim 12:
Reads:
12. The article of claim 12 wherein the article is chosen from a blown film, a cast film, a molded article, a melt-spun fiber, or an extruded article, wherein the extruded article is chosen form sheets, pipes, or tubes.

Should Read:
12. The article of claim 11 wherein the article is chosen from a blown film, a cast film, a molded article, a melt-spun fiber, or an extruded article, wherein the extruded article is chosen from sheets, pipes, or tubes.

Column 18, Claim 17:
Reads:
17. A polyethylene composition comprising:
    at least 50% by wt. of at least one polyethylene polymer chosen from a linear low density polyethylene polymer (LLDPE), a low density polyethylene polymer (LDPE), a high density polyethylene polymer (HDPE), or combinations thereof; and
    0.001 to 2% by wt nucleating agent comprising a structure of formulas (I), (II), or (III):

Signed and Sealed this
Twenty-second Day of October, 2019

Andrei Iancu
*Director of the United States Patent and Trademark Office*

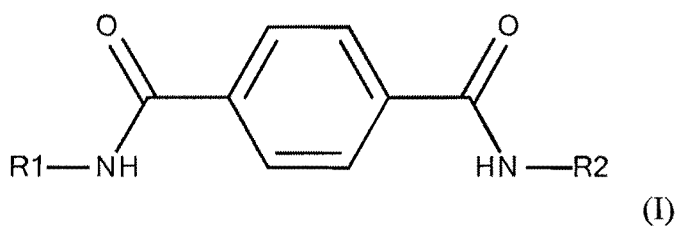

(I)

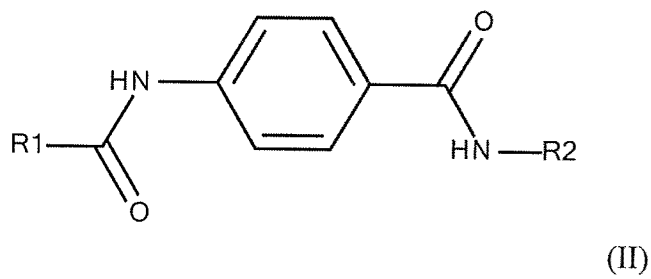

(II)

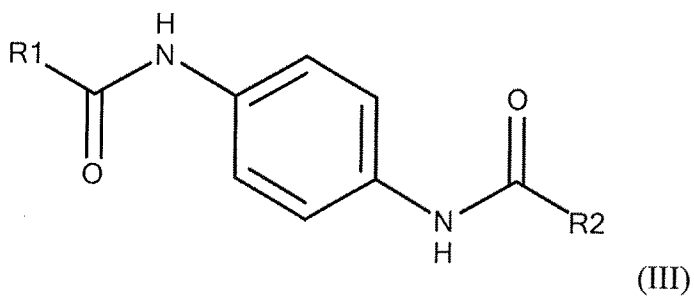

(III)

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; ($C_3$-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-$C12$ cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl;

naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl);

provided that when the nucleating agent is a structure of formula (II), R1 and R2 are not cyclohexyl;

wherein, when the polyethylene composition is used to form an article, the article has a haze value reduction of at least 15% when compared to an article having the same polyethylene polymer but free of the nucleating agent.

Should Read:
17. A polyethylene composition comprising:
    at least 50% by wt. of at least one polyethylene polymer chosen from a linear low density polyethylene polymer (LLDPE), a low density polyethylene polymer (LDPE), a high density polyethylene polymer (HDPE), or combinations thereof; and
    0.001 to 2% by wt nucleating agent comprising a structure of formulas (I), (II), or (III):

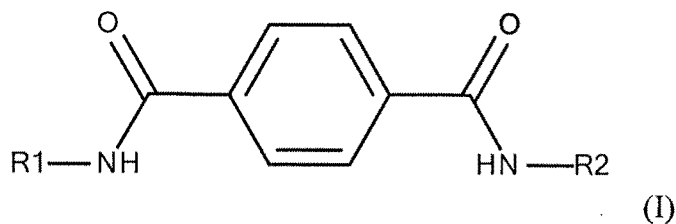

(I)

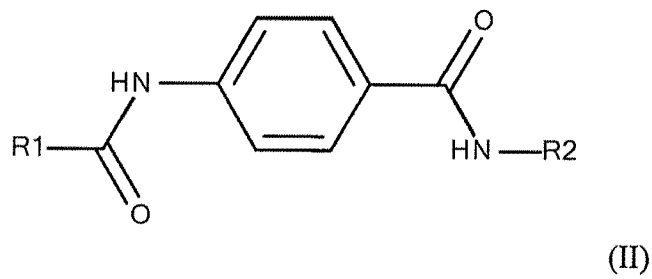

(II)

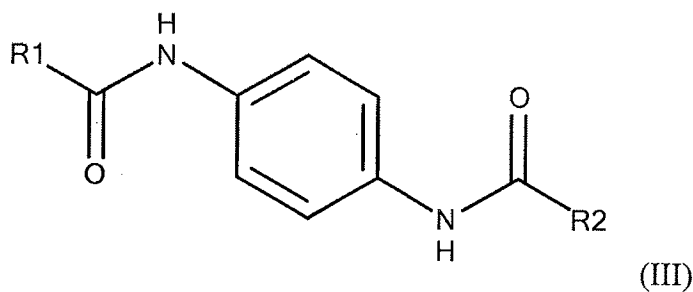

(III)

wherein R1 and R2 comprise the same or different moieties chosen from: $C_1$-$C_{20}$ alkyl unsubstituted or substituted by one or more hydroxy; $C_4$-$C_{20}$ alkenyl unsubstituted or substituted by one or more hydroxy; $C_2$-$C_{20}$ alkyl interrupted by oxygen or sulfur; $C_3$-$C_{12}$ cycloalkyl unsubstituted or substituted by one or more $C_1$-$C_{20}$ alkyl; (C3-$C_{12}$ cycloalkyl)-$C_1$-$C_{10}$ alkyl unsubstituted or substituted by one or more $C_1$-$C_{20}$ alkyl; bis[$C_3$-$C_{12}$ cycloalkyl]-$C_1$-$C_{10}$ alkyl unsubstituted or substituted by one or more $C_1$-$C_{20}$ alkyl; a bicyclic or tricyclic hydrocarbon radical with 5 to 20 carbon atoms unsubstituted or substituted by one or more $C_1$-$C_{20}$ alkyl; phenyl unsubstituted or substituted by one or more radicals selected from $C_1$-$C_{20}$ alkyl, $C_1$-$C_{20}$ alkoxy, $C_1$-$C_{20}$ alkylamino, di($C_1$-$C_{20}$ alkyl)amino, hydroxy and nitro; phenyl-$C_1$-$C_{20}$ alkyl unsubstituted or substituted by one or more radicals selected from $C_1$-$C_{20}$ alkyl, $C_3$-$C_{12}$ cycloalkyl, phenyl, $C_1$-$C_{20}$ alkoxy and hydroxy; phenylethenyl unsubstituted or substituted by one or more $C_1$-$C_{20}$ alkyl; biphenyl-($C_1$-$C_{10}$ alkyl) unsubstituted or substituted by one or more $C_1$-$C_{20}$ alkyl;
naphthyl unsubstituted or substituted by one or more $C_1$-$C_{20}$ alkyl; naphthyl-$C_1$-$C_{20}$ alkyl unsubstituted or substituted by one or more $C_1$-$C_{20}$ alkyl; naphthoxymethyl unsubstituted or substituted by one or more $C_1$-$C_2$ alkyl; biphenylenyl, flourenyl, anthryl; a 5-to-6-membered heterocylic radical unsubstituted or substituted by one or more $C_1$-$C_{20}$ alkyl; a $C_1$-$C_{20}$ hydrocarbon radical containing one or more halogen; or tri($C_1$-$C_{10}$ alkyl)silyl($C_1$-$C_{10}$ alkyl);
provided that when the nucleating agent is a structure of formula (II), R1 and R2 are not cyclohexyl;
wherein, when the polyethylene composition is used to form an article, the article has a haze value reduction of at least 15% when compared to an article having the same polyethylene polymer but free of the nucleating agent.

Column 19, Claim 18:
Reads:
18. The polyethylene composition according to claim 18, wherein when the nucleating is according to formula (I) and (III), R1, R2, or both are 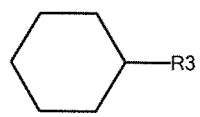 wherein R3 is a direct bond, or a $C_1$-$C_6$ alkyl or when the nucleating agent is according to formula (II), R1, R2, or both are 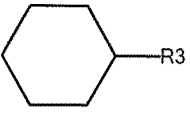 , wherein R3 is a $C_1$–$C_6$ alkyl.

Should Read:
18. The polyethylene composition according to claim 17, wherein when the nucleating agent is according to formula (I) and (III), R1, R2, or both are 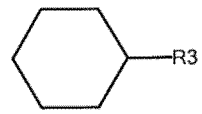 wherein R3 is a direct bond, or a $C_1$-$C_6$ alkyl or when the nucleating agent is according to formula (II), R1, R2, or both are 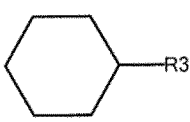 , wherein R3 is a $C_1$–$C_6$ alkyl.